United States Patent
Asaff Arancibia et al.

(10) Patent No.: US 9,943,496 B2
(45) Date of Patent: Apr. 17, 2018

(54) DIETARY SUPPLEMENT BASED ON ETHYL FERULATE

(71) Applicant: LABORATORIOS MINKAB, S. A. DE C. V., Tlalnepantla, Estado de Mexico (MX)

(72) Inventors: Jorge Selim Asaff Arancibia, Jalisco (MX); Angel Emilio Aceves Diez, Jalisco (MX); Humberto Gonzalez Rios, Sonora (MX); Rodrigo Nunes Pina, Qro (MX)

(73) Assignee: LABORATORIOS MINKAB, S. A. DE C. V., Tlalnepantla, Estado de Mexico (MX)

( * ) Notice: Subject to any disclaimer, the term of this patent is extended or adjusted under 35 U.S.C. 154(b) by 0 days.

(21) Appl. No.: 15/324,636

(22) PCT Filed: Jul. 23, 2015

(86) PCT No.: PCT/MX2015/000108
§ 371 (c)(1),
(2) Date: Jan. 6, 2017

(87) PCT Pub. No.: WO2017/014620
PCT Pub. Date: Jan. 26, 2017

(65) Prior Publication Data
US 2017/0202800 A1   Jul. 20, 2017

(51) Int. Cl.
| | |
|---|---|
| *A61K 31/235* | (2006.01) |
| *A23K 1/00* | (2006.01) |
| *A23L 1/30* | (2006.01) |
| *A61K 31/216* | (2006.01) |
| *A23K 50/10* | (2016.01) |
| *A23K 20/111* | (2016.01) |

(52) U.S. Cl.
CPC .......... *A61K 31/216* (2013.01); *A23K 20/111* (2016.05); *A23K 50/10* (2016.05)

(58) Field of Classification Search
CPC ....... A61K 31/216; A23K 1/14; A23K 1/1758
USPC ................. 514/532; 426/635, 648
See application file for complete search history.

(56) References Cited

U.S. PATENT DOCUMENTS

| | | | | |
|---|---|---|---|---|
| 3,617,299 A | * | 11/1971 | Mattoon ................. | A23K 40/30 424/442 |
| 5,447,953 A | * | 9/1995 | Isler ..................... | A61K 31/365 424/115 |
| 6,248,374 B1 | * | 6/2001 | Murray .................. | A23K 10/30 426/623 |
| 2009/0220648 A1 | * | 9/2009 | Nilsson .................. | A23K 20/24 426/72 |
| 2014/0004195 A1 | * | 1/2014 | Fahrenholz ............ | A23K 40/10 424/489 |
| 2014/0370106 A1 | * | 12/2014 | Funda .................. | A61K 9/1658 424/490 |

OTHER PUBLICATIONS

International Search Report for PCT/MX2015/000108, English translation attached to original, Both completed by the Spanish Patent Office dated Oct. 20, 2015, All together 6 Pages.
Website CIAD Dated Oct. 28, 2013, 2 Pages, Retrieved from Internet, URL: http://www.ciad/mx/rss/946-carne-molida.html, "Logra CIAD prolongar the vida of anaquel from carne molida of res" English Translation of Title: "CIAD Achieves Shelf Life of Ground Beef".
Reyes et al. "Antifungal activity of ethyl ferulate" 2 Pages, 2011 Retrieved from Internet URL: http://www.smbb.com.mx/congress%20smbb/cancun13/TRABAJOS/SMBB/BiotecnologiaAgricolaVegetal/11-024.pdf.
Warner et al. Jacos 2005, vol. 82, No. 9, pp. 647-652, "Addition of ferulic acid, ethyl ferulate, and feruloylated nonoacyl and diacylglycerols to salad oils and frying oils".
Caicedo et al. Argentine Animal Production Site 2011, Google English Translation attached to original, All together 13 Pages, "Effects of Beta-Agonists (Clenbuterol), In the Fisio-Hepaic and Reproductive in Ruminants".
Pringle et al. J. Anim. Sci. 1993, vol. 71, pp. 636-644, Published Dec. 11, 2014, "Effects over Time of Feeding a B-Adrenergic Agonist to Wether Lambs on Animal Performance, Muscle Growth, Endogenous Muscle Proteinase Activities, and Meat Tenderness1,2".
Strydom et al. Meat Science 2009, vol. 81, No. 3, pp. 557-564, "The comparison of three β-agonists for growth performance, carcass characteristics and meat quality of feedlot cattle".
Avendano-Reyes et al. Journal of animal science 2006, vol. 84, pp. 3259-3265, "Effects of two B-adrenergic agonists on finishing performance, carcass characteristics, and meat quality of feedlot steers 1,2".
Mattila et al. Journal of Food Composition and Analysis 2007, vol. 20, pp. 152-160, "Phenolic acids in potatoes, vegetables, and some of their products".
Nirmal et al. Food Chemistry 2009, vol. 116, No. 1, pp. 323-331, "Effect of ferulic acid on inhibition of 20 polyphenoloxidase and quality changes of Pacific white shrimp (*Litopenaeus vannamei*) during iced storage".
Masuda et al. Food Sci. Technol. Res. 2006, vol. 12, No. 3, pp. 173-177, "Antioxidant Mechanism Studies on Ferulic Acid: Isolation and Structure Identification of the Main Antioxidation Product from Methyl Ferulate".
Ergun et al. Arch. Pharm. Res. 2011, vol. 34, No. 8, pp. 1251-1261, "Synthesis, Antioxidant and Antimicrobial Evaluation of Simple Aromatic Esters of Ferulic Acid".

(Continued)

*Primary Examiner* — Raymond Henley, III
(74) *Attorney, Agent, or Firm* — Brooks Kushman P.C.

(57) ABSTRACT

Nutritional supplement, feed formulation and methods to improve the efficiency of meat production of a bovine animal, using ethyl ferulate as a nutritional supplement; where the administration of ethyl ferulate at bovine animal, is premixed with an excipient food grade, feed formulation, balanced food, concentrated food, and the like. The ethyl ferulate administration is daily during the final stage of fattening bovine animal, wherein the final stage of fattening is 20 to 40 last days.

18 Claims, 8 Drawing Sheets

(56) References Cited

OTHER PUBLICATIONS

Pfalzgraf et al. Journal of Agricultural and Food Chemistry 1995, vol. 43, pp. 1339-1342, "A-tocopherol Contents and Lipid Oxidation in Pork Muscle and Adipose Tissue during storage".

American Meat Science Association AMSA, Chicago, Illinois, USA, 1995, 28 Pages, "Research Guidelines for Cookery, Sensory Evaluation and Instrumental Tenderness Measurements of Fresh Meat".

McLellan et al. Journal of Food Quality 1995, vol. 81, pp. 235-240, "Hue angle determinations and statistical analysis for multiquadrant Hunter L, a, b Data".

Pollorena et al. Thesis of master in Science. Center for Research in Food and Development A.C. Hermosillo, Sonora, Mexico 2012, English Google Machine Translation attached to original, All togehter 94 Pages, "Antioxidant and antimicrobial capacity of leaf extracts of Agave angustifolia Haw and its effect on the quality of beef burgers".

Stewart et al. Journal of Food Science 1965, vol. 30, No. 3, pp. 464-469, "The Use of Reflectance 10 Spectrophotometry for the Assay of Raw Meat Pigments".

Sutton et al. Meat Science 1997, vol. 46, No. 2, 173-180, "Influence of Slaughter Weight Stress Gene Genotype on the Water-holding Capacity and Protein Gel Characteristics of Three Porcine Muscles".

Platt et al. Department of Animal and Food Sciences, Texas Tech University 2012, 1 Page, "The effect of ferulic acid on myogenic regulators of growth in bovine satellite cells".

Zhang et al. Synthetic Communications 1998, vol. 28, No. 7, pp. 1159-1162, "Fe2(SO4)3xH2O Catalytic Esterification of Aliphatic Carboxylic Acids with Alcohols".

Li, Synthetic Communications 1999, vol. 29, No. 22, pp. 3901-3903, "Catalytic Esterifications of Carboxylic Acids and Alcohols by Sodium Bisulfate Monohydrate".

United States Department of Agriculture, Agricultural Marketing Service, Livestock, Poultry and Seed Program, Effective Date Mar. 1, 2016, 17 Pages, "United States Standards for Grades of Carcass Beef".

Tatum, Department of Animal Science, Colorado State University 2007, 4 Pages, "Beef Grading".

Pedro Abraham Sema Guerrero et al., Unpublished Master's Thesis in Science, Center for Research in Food and Development, Hermosillo, Sonora 2012, English Machine Translation of First Page and English Abstract attached to original, All together 91 Pages, "Impact of ferulic acid supplementation on the quality of commercial bovine meat".

David Roman Sanchez Chipres et al. University Center of Biological and Agricultural Sciences, University of Guadalajara, F.E.S Cuautitlan, UNAM, Minkab Mexicana S.A. De C.V. Jan. 2011, English Machine Translation of First Page attached to original, All together 12 Pages, "Effect of Ferulic Acid on the Grease Thickness Dorsal in Pigs".

Website: www.ncss.com Retrieved from the Wayback Machine on Nov. 11, 2017, Dated Nov. 19 2012, All together 4 Pages, "NCSS Statistical Software".

\* cited by examiner

DIETARY SUPPLEMENT BASED ON ETHYL FERULATE

CROSS-REFERENCE TO RELATED APPLICATION

This application is the U.S. national phase of PCT Application No. PCT/MX2015/000108 filed on Jul. 23, 2015, the disclosure of which is incorporated in its entirety by reference herein.

TECHNICAL FIELD OF THE INVENTION

The present invention relates to the technical fields of chemical and food, specifically with the branch of dietary supplements as it provides the use of ethyl ferulate as a food supplement; a pre-feed mixture containing ethyl ferulate; a nutritional formulation containing ethyl ferulate and a method for improving the efficiency of meat production in cattle fattening.

BACKGROUND OF THE INVENTION

Today the increase in world population, has resulted in increased demand for food, especially protein products of animal origin (Caicedo et al., 2011). Therefore, the livestock industry has implemented the use of growth-promoting compounds, in order to improve feed efficiency, achieve better daily weight gain, which gives result in increased production and reduced costs. Among the most commonly used promoters are growth hormone implants and β-adrenergic agonists compounds (BAA) (Eng, 2000).

The BAA are analogs of catecholamines hormones, and are known for their action to increase muscle accretion, and decrease fat synthesis (Pringle et al., 1993). Currently, these compounds are widely used to promote growth in cattle and pigs (Strydom et al., 2009) due to greater weight gain and feed efficiency is obtained, thus achieving a reduction in production costs.

However, the impact of animal production BAA has taken two ways, one is the benefits they have in animal production and procurement of more lean meat; but there are also risks of poisoning by eating meat and offal of animals supplemented with BAA prohibited, in addition to producing more meat texture and a darker color (Avendaño et al., 2006).

Ferulic acid (FA), is a phenolic compound that is part of the cell wall in plants, whose content varies according to the species. This phenolic compound has been extracted from rice bran and corn, wheat bran and beet pulp (Mattila and Hellström, 2007), and has shown to have a high potential for use in the food industry because of their bioactive properties (Child-Medina, Carvajal-Millan, Gardea-Bejar, Rascon-Chu, & Marquez-Escalante, s/f). The food industry has implemented as an antioxidant agent, achieving retard oxidation of lipids (Nirmal and Benjakul, 2009).

AF, in addition to its antioxidant and antimicrobial capacity, it is attributed growth promoting effect because it has a similar chemical structure to commercial BAA used in livestock (Sanchez et al, 2011; Serna, 2012). Recently, an in vitro study with bovine satellite cells showed that AF is recognized by β receptors on the cell membrane and showed similar levels of mRNA abundance of commercial BAA zilpaterol hydrochloride (Platt et al., 2012).

Sanchez et al. (2011) were supplemented with 50 ppm of AF swine confinement, and observed a decrease in back fat thickness over the control group. In another study, Serna (2012) tested the dietary supplementation of 6 ppm of AF in cattle over the last 30 and 60 days of feedlot phase and compared against a commercial BAA and a control group, and noted that meat from cattle supplemented for 30 days lipid oxidation slowed and kept the red color of the meat for a longer time compared to the control.

Furthermore, this meat was softer than the BAA group. However, in the productive performance of the animals is not a promoting effect as significant growth as that obtained with the commercial BAA was reflected.

The ethyl ferulate (FE), AF ester, and etanol, may be obtained by chemical or enzymatic catalysis (Zhang, 1998; Li, 1999). Meanwhile, Masuda et al. (2006) and Ergün et al. (2011) have reported that ethyl ferulate has antibacterial and antioxidant capacity very similar to those of ferulic acid. Similarly, most chemical into fatty media, affinity supports their integration in a wide variety of foods. These considerations make a good choice for FE used as an antioxidant and promoter of growth from animal production.

Therefore, this invention has as main objective to evaluate the effect of supplementation with low doses (5 ppm) and high doses (10 ppm) of ethyl ferulate (FE) on productive performance and meat quality in cattle producers of meat.

DISCLOSURE OF THE INVENTION

The characteristic details of the invention are shown in the following description, figures and examples, which are accompanied, by way of illustrating the embodiment of the invention, which should not be considered as limiting the present invention. So all those variants that are obvious to one skilled in the art, fall within the scope of this invention.

DEFINITIONS

Figure 1:
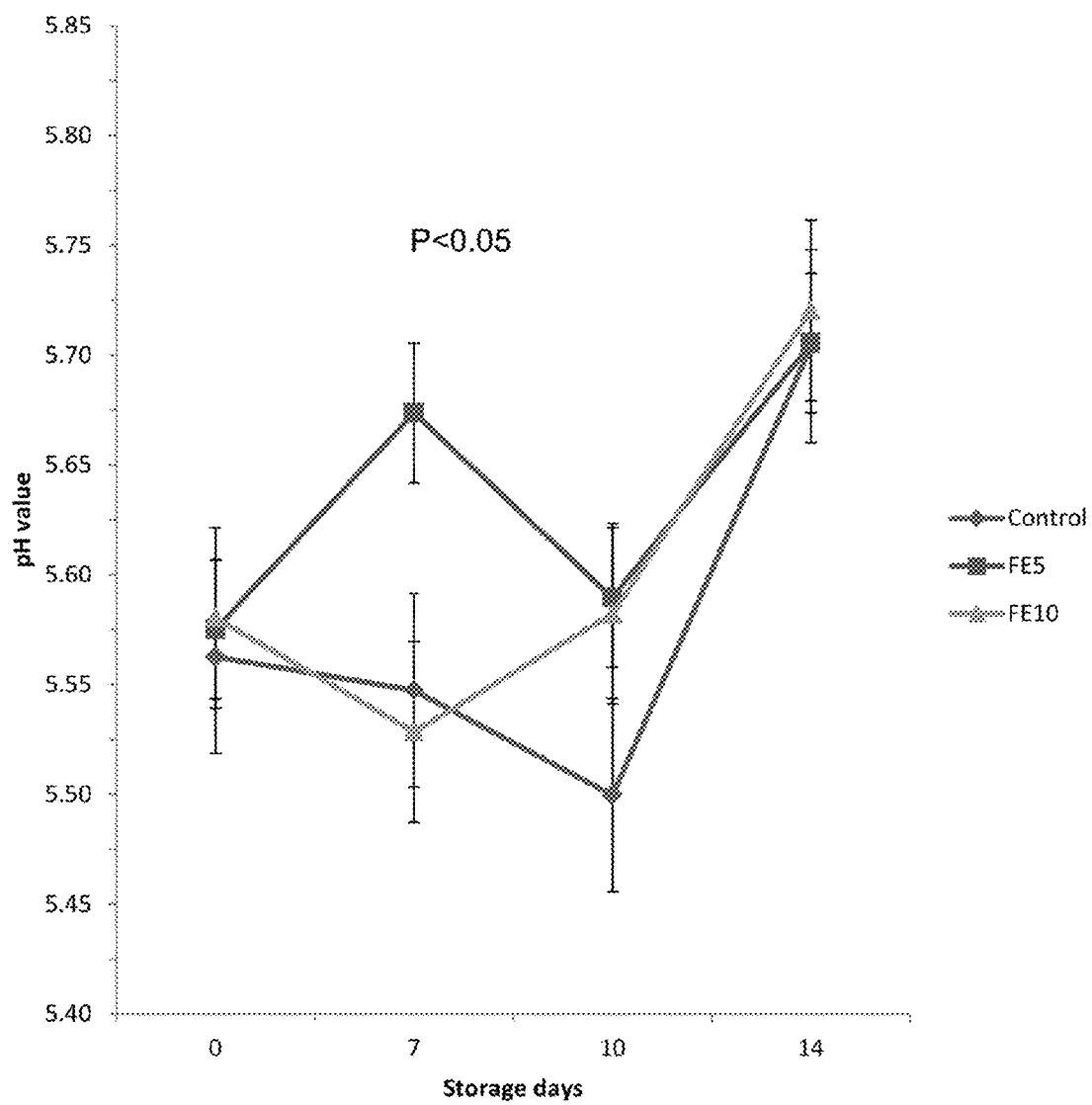
FIG. 1. pH values of beef during refrigerated storage at 4° C.

For a better understanding of the terminology used in this description, then it is a definition and/or explanation of the terms used, which are merely explanatory and not limiting.

"Balanced food" is that mixture of ingredients whose nutritional composition can provide the amount of bioavailable nutrients needed to meet the requirement of the metabolism of an animal, depending on your metabolic stage, age and weight.

"Average daily food consumption" (CDP) refers to food intake of the animal per day, usually expressed in terms of dry matter content.

"Daily weight gain" (GDP) refers to increased body weight (kg)/number of days.

"Feed Conversion" (CA)=CDP/GDP. Improved feed conversion means a decrease in the ratio of CDP/GDP.

"Hot carcass weight (PCC)" is the "hot" weight (not frozen) in kilograms carcass, taken after slaughter and after the skin, head, intestinal tract and internal organs have been removed.

"Cold carcass weight (PCF)" is the carcass weight in kilograms taken after 24 hours of cooling at 4° C.

"Carcass yield" is determined by dividing the weight of the hot runner from the final live weight, and then multiplying by 100.

"Marbling" refers to deposition or intramuscular fat content is determined according to the guidelines of the USDA (2000): Trace (300-399), Light (400-499), Little (500-599) Modesto (600-699), Moderate (700-799), slightly abundant (800-899).

"Classification of the carcass" refers to the classification of meat quality on the scale proposed by the USDA (2000), based on the degree of marbling and carcass physiological maturity: Selecta – (400-449), Selecta + (450-499) Choice – (500-599), half Choice (600-699), Choice + (700-799), Prime (800 or greater).

"Improving the efficiency of meat production" means improving one or more of the variables live performance GDP growth and CA or amelioration of one or more of the variables of the carcass PCC, PCF, carcass yield, area of rib eye, marbling and classification of a bovine animal that is dieted with a food containing Ethyl ferulate (FE) compared to a bovine animal that is fed without FE.

"Bovine animal" means an animal of the genus *Bos taurus* or *Bos indicus*, especially cattle, buffalo, zebu and yak, more particularly cattle, which are raised to produce meat for human consumption, specifically, heifers, steers, cows and bulls.

"Metric ton (TM)" is a unit of measurement of mass equal to 1,000 kg.

"Ppm" is an abbreviation for parts per million, ppm is a value that represents the part of an integer in units of $1/1000000$. "Ppm" is a dimensionless quantity, a 2 quantities of the same unit. For example, a concentration of 5 ppm FE means 5 mg FE per kg body weight of bovine animal. In another example a concentration of 10 ppm FE means 10 mg FE per kg body weight of bovine animal.

"Premix" with this term we mean a combination of an amount of ethyl ferulate with an amount of a food grade excipient.

The present invention relates to the use of ethyl ferulate as a nutritional supplement, more specifically for administration to a bovine animal feedlot, in order to improve the efficiency of meat production.

As an object of the present invention is a feed premix to a bovine animal; wherein said premix comprises an amount of ethyl ferulate and a food grade excipient.

Another object of the present invention is a food formulation for a bovine animal, which comprises an amount of ethyl ferulate and a food; wherein the amount of ethyl ferulate may be 100 to 600 g per ton of feed (TM); where a preferred embodiment is that the food formulation has a ethyl ferulate amount of 200 to 500 g/TM.

In another embodiments of the present invention it is that both the feed premix and feed formulation containing ethyl ferulate, may be administered to a bovine animal, which belongs to the subspecies: *Bos primigenius* taurus and *Bos primigenius indicus*.

The feed formulation comprising ethyl ferulate according to the present invention, where food can be a balanced food, fattening balanced food, concentrated food, to name some examples, but not limited way.

A further aspect of the present invention is a method for improving the efficiency of meat production in a bovine animal, said method comprising feeding the animal a bovine daily nutritional formulation that contains a dose ethyl ferulate, during the last days of fattening phase of the bovine animal. Where an embodiment of this method is that the amount of ethyl ferulate is 5 to 10 ppm; more preferably still 10 ppm.

The method for improving the efficiency of meat production of the present invention can be applied in a bovine animal, which belongs to the subspecies: *Bos primigenius taurus* y *Bos primigenius indicus*.

In one embodiment of the aforementioned method it is that the ethyl ferulate is provided on the last day of the phase of fattening bovine animals; preferably it is from 20 to 40 days; even more preferred at 30 days.

A further embodiment of the method in question is the ethyl ferulate is applied to feed formulation, pure or premixed, according to the feed premix described above.

Therefore, another object of the present invention is the use of ethyl ferulate as a nutritional supplement to a bovine animal, to enhance meat production.

EXAMPLE

This example is a mere embodiment of the present invention, which should not be considered as limiting the invention, but rather is illustrative only.

A study was conducted to verify the effect of dietary supplementation of ethyl ferulate on productive performance, carcass quality and meat heifers completion, where the objective was to evaluate the effect of supplementation of two concentrations (5 and 10 ppm) ethyl ferulate on productive performance, carcass quality and meat of beef cattle.

Behavioral Test.

Animals and Management

Productive performance test was conducted in the feedlot of a commercial farm, located in the state of Sonora, Mexico, at an altitude of 210 meters above sea level, latitude 29° 05' 56" and longitude 110° 57' 15" (INEGI, 2012).

Prior to the start of the study, 270 cattle (heifers) commercial beef producers crosses (of racial influence mainly *Bos taurus*), which were divided into three lots with uniform power days, racial origin and composition were selected. The animals were weighed individually and identified with plastic earring different color, to be distributed randomly according to a block design (3) complete random. To facilitate the handling of heifers and scheduling your humane slaughter, each block was postponed one week and was formed by three pens with 30 animals each.

Experimental Treatments.

Once done animals blocks, each pen within each block was completely randomized one of the following treatments:

Treatment CONT: Animals receiving the basal diet without additive (control).

Treatment FE5: Animals receiving the basal diet supplemented the last 30 days of fattening stage 5 ppm of ethyl ferulate.

Treatment FE10: Animals receiving the basal diet supplemented the last 30 days of the fattening phase with 10 ppm of ethyl ferulate.

Feeding and Performance Test.

The initial live weight of the animals was 484.68±2.84 kg. All animals were fed a basal diet with a ratio of forage:

concentrate of 20:80, which was formulated to contain 1.62 Mcal of net energy gain/kg of feed, 12.7% crude protein, 0.91% Calcium and 0.27% phosphorus. The amount of ethyl ferulate per ton of feed was first added to the mineral premix and later it was incorporated into the automated experimental ration.

All animals were individually weighed at the beginning and end of the experimental test, for which an electronic scale Tru-Test 300 (Tru-Test Corporation, New Zealand) equipped with recording memory was used. Daily weight gain (GDP) was estimated by the difference between initial and final weight and divided by 30 (the feeding period).

Feed intake was recorded daily for corral, for which both the food offered and refused was weighed. Feed conversion per pen/treatment with the average food consumption ratio between GDP was also calculated.

Sacrifice and Evaluation of Carcass Quality.

Once the productive performance test was finished, the animals were sacrificed following the current regulations.

The pH was measured at 45 min and 24 h postmortem in the *Longissimus dorsi* (LD) at the 12th intercostal space using a portable digital potentiometer brand HANNA HI 99163 (Mettler-Toledo Process Analytical Inc., Wilmington, Mass., USA). The weight of the hot carcass was recorded, then the carcasses were cooled to 0° C. for 24 h.

At 24 h postmortem the weight of the cold carcass was measured. In at least 36 carcasses per treatment, area in cm$^2$ rib eye, the thickness of back fat in mm, was evaluated. The degree of marbling was also evaluated following USDA guidelines (2000): Trace (300-399), Light (400-499), Little (500-599), Modest (600-699), Moderate (700-799), Slightly abundant (800-899). These determinations were made in the LD muscle to level 12th intercostal space. Finally, the quality level of the channel according to USDA (2000) was estimated, based on the degree of marbling and carcass physiological maturity: Select − (400-449), Select + (450-499) Choice − (500-599), Choice medium (600-699), Choice + (700-799), Prime (800 or greater).

Samples for Shelf Life Study

Between 24 and 36 h postmortem, carcasses were deboned and randomly selected 18 channels per treatment (n=6 per treatment/block) to sample meat (thoracic part of LD, cut ribeye left channel). The meat samples were identified, vacuum packed and frozen at −18° C. for about 15 days. Twenty-four hours before the respective shelf life analysis, the samples were placed in a cooling chamber at 4° C. for thawing. Later, they were cut 5 slices of 1.5 cm, always following the same order of cutting (side flow to the front of the LD muscle).

Shelf Life Study.

In order to evaluate the antioxidant effect of the additives supplied, 5 chops each experimental unit of the respective treatments were taken, which were packed with traditional packing (stretch wrap) and subjected to a cooling process at 4° C. for 9 days in the presence of light.

During the shelf life was evaluated (day 0, 7, 10 and 14 storage) color parameters and the determination of reactive substances, such as thiobarbituric acid (TBARS) and percentage of metmyoglobin.

Determination of Color:

To measure the parameters of meat color from each treatment Minolta colorimeter (Chroma meter model CR-400, Konica Minolta Sensing, Inc., Japan) was used. The color determination included the L values, measuring the brightness of the product which can vary from 100 for perfect white to 0 for black; the a value measuring of the red color, the b value determines the yellow (tendency of fat deposition); in addition, the hue angle using the formula tan-1 (b/a) (McLelland et al., 1995) was estimated. Color determination was made on the surface of specimens cold (4-6° C.) in 5 different positions of the sample.

For the determination of pH, HANNA portable digital potentiometer is used with penetration electrode and thermometer HANNA HI 99163, (Mettler-Toledo Process Analytical Inc., Wilmington, Mass., USA). Three measurements per sample were performed.

Lipid Oxidation and Percentage of Metmyoglobin

Determining Lipid Oxidation.

Lipid oxidation was performed by determining the reactive substances at acid 2-thiobarbituric (TBARS, for its acronym in English), according to the methodology described by Pfalzgraf et al. (1995). The process began with the homogenization of 5 g sample with 15 mL of trichloroacetic acid. This was done with the aid of an Ultra Turrax homogenizer (T25, IKA-Werke, USA) at a speed of 11,000 rpm for 1 min. The temperature rise is avoided, keeping the tubes on ice to prevent lipid oxidation.

After homogenizing the sample, filtered with filter paper No. 42 (Whatman International, Maidstone, England) and took 2 mL of filtrate, which are mixed in test tubes containing 2 mL of a 20 mM solution of TBA freshly prepared. Subsequently the tubes were homogenized for 30 s with rotatubos (M G-560, VWR, Bohemia, N.Y. USA) and heated at 97° C. for 20 min in a water bath to allow color development. Once carried out the previous step, the tubes were cooled on ice and proceeded to read the samples at 532 nm using a spectrophotometer Spectronic Genesis 5 model 336001 (Thermo Electron Corporation, USA). The results were calculated using a calibration curve using 1,1,3,3, tetramethoxypropane (TMP) and expressed as reactive 2-thiobarbituric acid reactive substances in mg malonaldehyde/kg sample.

Metmyoglobin Analysis:

The percentage of metmyoglobin formation during storage, was measured at the surface of meat, according to the method of Steward et al. (1965). It was determined by the spectrophotometric measurement of the reflectance at wavelengths of 525 and 572 nm with a Minolta CM 2600d spectrophotometer and the K/S ratio was calculated. The average reading is each 5 measurements on the surface of the meat.

Experimental Design and Statistical Analysis.

Productive performance data were analyzed by ANOVA with a design of a randomized complete block using the method of generalized linear models (GLM) using initial weight as a covariate; data carcass quality were analyzed under a completely randomized design blocks. The variance analysis (mixed models procedure), included as a fixed effect to experimental treatments and as a random effect the initial weight of animals for productive performance data and final weight for carcass quality. The study data shelf life was analyzed using analysis of variance of two ways, considering the fixed effects of treatment and storage time. When differences between treatments were detected in productive performance variables and carcass quality, comparisons of means were performed by orthogonal contrasts. The following contrasts were tested: Contrast 1: Control vs FE5+FE10; Contrast 2: FE5 vs FE10. For data quality meat in the study of oxidative stability, the comparison of means was by the Tukey test. All data were processed in the statistical package NCSS (NCSS Version 8.0, 2012).

Results Obtained

Productive Behavior

Table 1 shows the effects of supplementation of ethyl ferulate (FE) on productive performance of heifers in completion are presented. The initial body weight was similar for all treatments, which ranged from 483.1-485.4 kg, indicating that animals were drawn appropriately for each experimental group. The final live weight was affected by treatments (P<0.05), but no observed effects between doses (P>0.05).

With respect to daily gain (GDP) an increase 26% (P<0.05) was observed in animals that were supplemented with FE, relative to control (contrast C1). This demonstrates a growth promoting effect by supplementation of the compound in the diet of heifers completion.

TABLE 1

Productive performance of heifers (mean ± standard error) supplemented with ethyl ferulate during the last 30 days of intensive feeding.

| | Treatments* | | |
|---|---|---|---|
| | Control | FE5 | FE10 |
| N | 90 | 89 | 88 |
| Initial weight, kg | 485.48 ± 4.9 | 485.39 ± 4.8 | 483.14 ± 5.0 |
| Final weight, kg$^a$ | 513.62 ± 5.2 | 519.58 ± 5.4 | 520.20 ± 5.63 |
| Daily gain, kg$^a$ | 0.93 ± 0.04 | 1.13 ± 0.04 | 1.23 ± 0.04 |
| Feed intake, kg$^a$ | 7.61 ± 0.04 | 8.11 ± 0.07 | 8.09 ± 0.07 |
| Feed conversion, kg$^a$ | 12.25 ± 1.6 | 8.78 ± 0.6 | 7.25 ± 0.27 |

*Control: without additive; FE5: ethyl ferulate 5 ppm/day; FE10: ethyl ferulate 10 ppm/day.
$^a$contrast 1: Control vs FE5 + FE10 (P < 0.05).
$^b$Contrast 2: FE5 vs FE10 (P < 0.05).

With regard to food consumption, FE supplementation affected this variable (P<0.05). Daily food consumption fluctuated around 8 kg. An important aspect of all livestock is the calculation of feed conversion, as this depends partly on the profitability of this activity. In this regard, it should be noted that this variable was significantly affected by the treatments (P<0.05). An improvement of 35% in feed conversion (P<0.05) in the supplemented with FE in the control group (Contrast C1) animals was observed, indicating that heifers that were supplemented with FE required 4.3 kg less feed to gain one kilogram of live weight.

Carcass Quality

The carcass characteristics of heifers supplemented with ethyl ferulate (FE) the last 30 days of intensive feeding are presented in Table 2. In general, we observed that FE affects most carcass characteristics evaluated. The hot carcass weight (PCC) of heifers supplemented with 1.80% FE was greater (P<0.001) than those produced by the control animals. This represents more than 5 kg increase in carcass weight.

TABLE 2

Characteristics of the channel heifers (mean ± standard error) supplemented with ethyl ferulate the last 30 days of intensive feeding.

| | Treatments* | | |
|---|---|---|---|
| | Control | FE5 | FE10 |
| N | 90 | 89 | 88 |
| Initial weight, kg | 485.48 ± 4.9 | 485.39 ± 4.8 | 483.14 ± 5.0 |

TABLE 2-continued

Characteristics of the channel heifers (mean ± standard error) supplemented with ethyl ferulate the last 30 days of intensive feeding.

| | Treatments* | | |
|---|---|---|---|
| | Control | FE5 | FE10 |
| Final weight, kg$^a$ | 513.62 ± 5.2 | 519.58 ± 5.4 | 520.20 ± 5.63 |
| Hot carcass weight, kg$^a$ | 318.34 ± 3.1 | 323.97 ± 3.25 | 324.19 ± 3.23 |
| Cold carcass weight, kg$^a$ | 315.23 ± 3.1 | 320.81 ± 3.25 | 320.50 ± 3.19 |
| pH 45 min postmortem | 6.74 ± 0.2 | 6.71 ± 0.1 | 6.72 ± 0.1 |
| pH 24 h postmortem | 5.50 ± 0.3 | 5.56 ± 0.2 | 5.52 ± 0.2 |
| Hot yield carcass, %$^a$ | 62.01 ± 0.16 | 62.38 ± 0.15 | 62.39 ± 0.19 |
| Cold carcass yield, % | 61.40 ± 0.16 | 61.77 ± 0.16 | 61.68 ± 0.19 |
| Rib eye area, (cm$^2$) | 86.60 ± 1.87 | 85.67 ± 2.28 | 86.60 ± 1.87 |
| Backfat, mm | 13.32 ± 1.19 | 14.60 ± 1.05 | 15.82 ± 0.84 |
| Marbling**$^{*a,b}$ | 554.41 ± 15 | 578.57 ± 16 | 637.14 ± 15 |
| % de Choice or greater$^c$ | 48.5 | 66.7 | 80 |

*Control: without additive; FE5: ethyl ferulate 5 ppm/day; FE10: ethyl ferulate 10 ppm/day.
**Marbling: Traces (300-399), Light (400-499), Little (500-599), Modesto (600-699), Moderate (700-799).
$^a$Contrast 1: Control vs FE5 + FE10 (P < 0.05).
$^b$Contrast 2: FE5 vs FE10 (P < 0.05).
$^c$Percentage carcass Choice are different between treatments (P < 0.05). Chi-square (X$^2$ = 12.85 Value 4 gl).

As the cold carcass weight (PCF) the same effect was observed for PCC, as was an increase of 1.86% on carcasses of animals supplemented with FE (P<0.05) than those obtained in the control group.

Regarding the yield percentages in hot carcass and cold carcass, there was no effect for treatment (P>0.05), however, because the animals supplemented with FE presented heavier carcass, this affects in greater quantity of meat useful for sale.

The thickness of the dorsal fat was not affected by treatments (P>0.05). Values were in the range of 13 to 15 mm of backfat. These values are within the expected weight range of carcass produced. The marbling or intramuscular fat deposition was affected by treatments (P<0.05). More marbling appeared in the carcass of the supplemented animals compared to non supplemented. The animals supplemented with 10 ppm FE had a higher marbling regarding supplemented with 5 ppm FE animals.

Regarding the degree of carcass quality, differences (P<0.05) between treatments in the percentage of carcass classified as Choice or higher is detected. It was observed that control treatment presented a Choice carcass 48.5%, while treatment with 10 ppm/day FE presented 80% Choice.

The findings of carcass quality indicate that FE supplementation produced carcass with more marbling, and therefore a higher percentage of Choice carcass. The favorable effect on fat deposition showed FE, indicates an opposite effect to anabolic agents for this feature.

Shelf Life Study Meat pH Meat

FIG. 1 shows the behavior of the meat pH over time of refrigerated storage. No differences between treatments (P>0.05) and the mean values were within the pH normal range for fresh meat (5.5-5.8).

CIE Color Parameters L*a*b*

Figure 2:
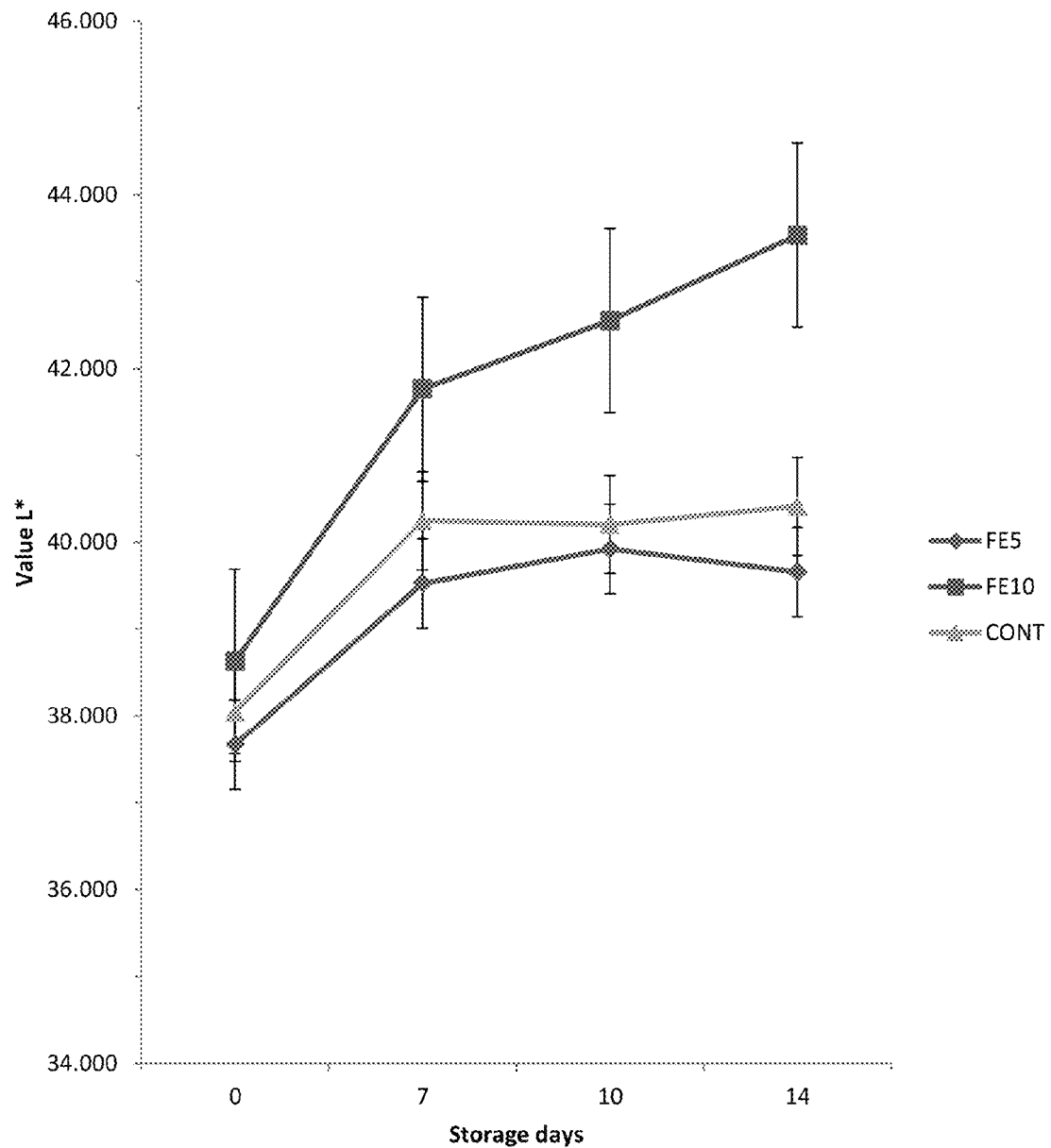
FIG. 2. Performance parameter color L* of beef during refrigerated storage at 4° C.

The color characteristics of the meat are shown in FIGS. 2 to 6. The color parameter L* (lightness) was affected by the dietary treatments (P<0.05). The meat of the control animals and the supplemented animals 5 ppm FE, presented lower brightness values and were different (P<0.05) than those observed in meat from animals supplemented with 10 ppm of FE that presented the highest values (FIG. 2).

Figure 3:
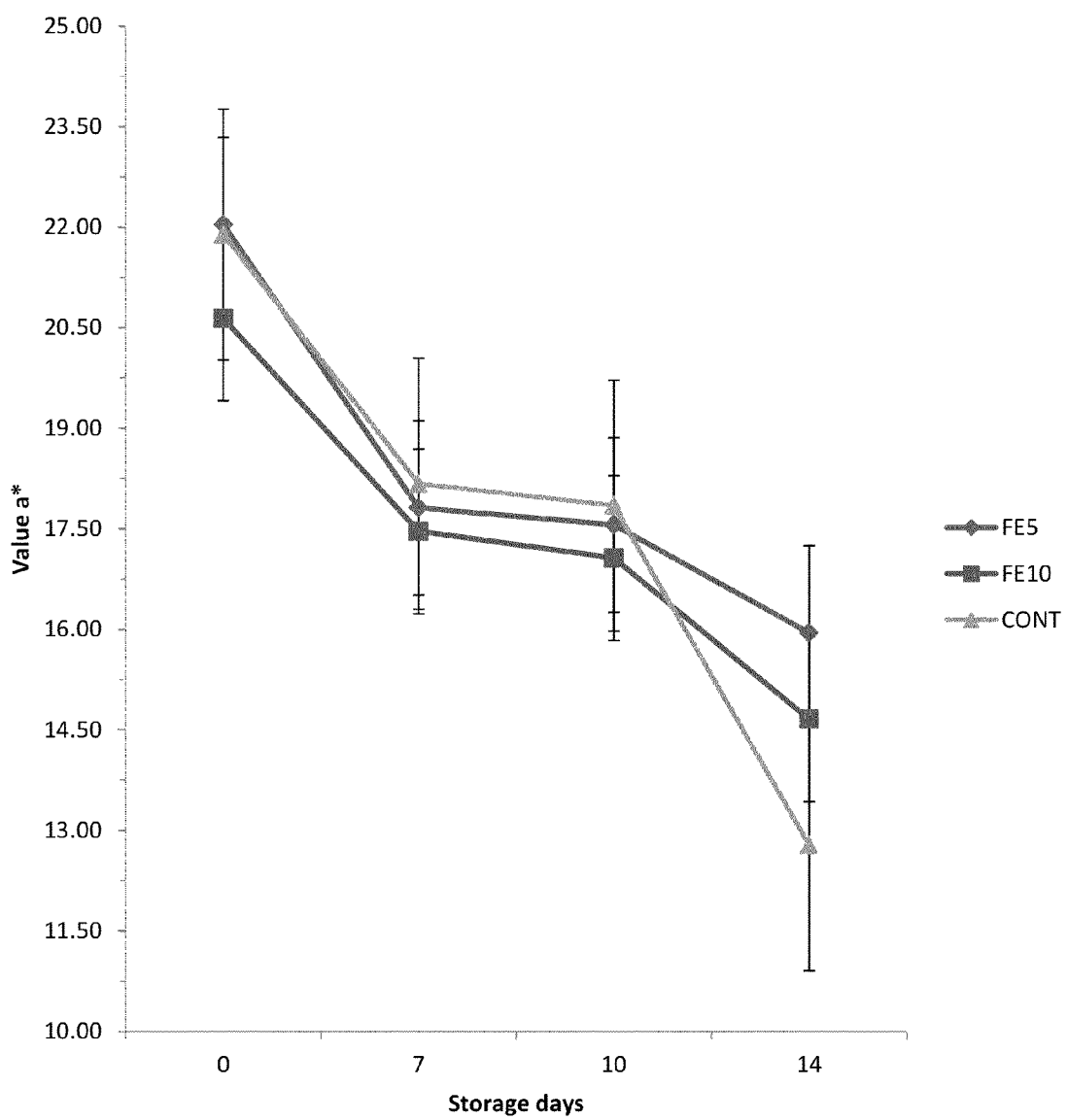
FIG. 3. Performance parameter color a* of beef during refrigerated storage at 4° C.
Figure 4:
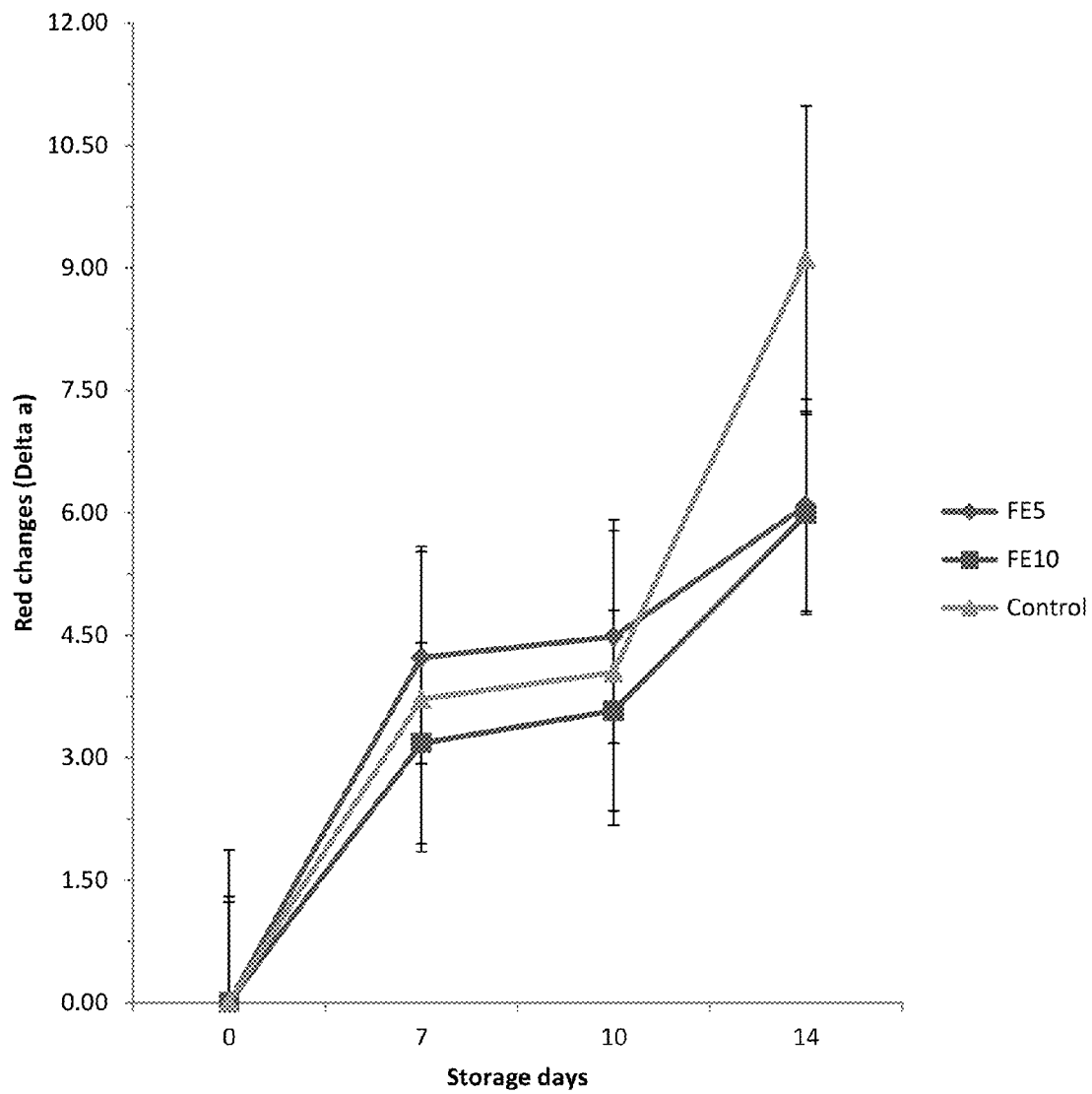
FIG. 4. Changes red (Δa*) of beef during refrigerated storage at 4° C.
Figure 5:
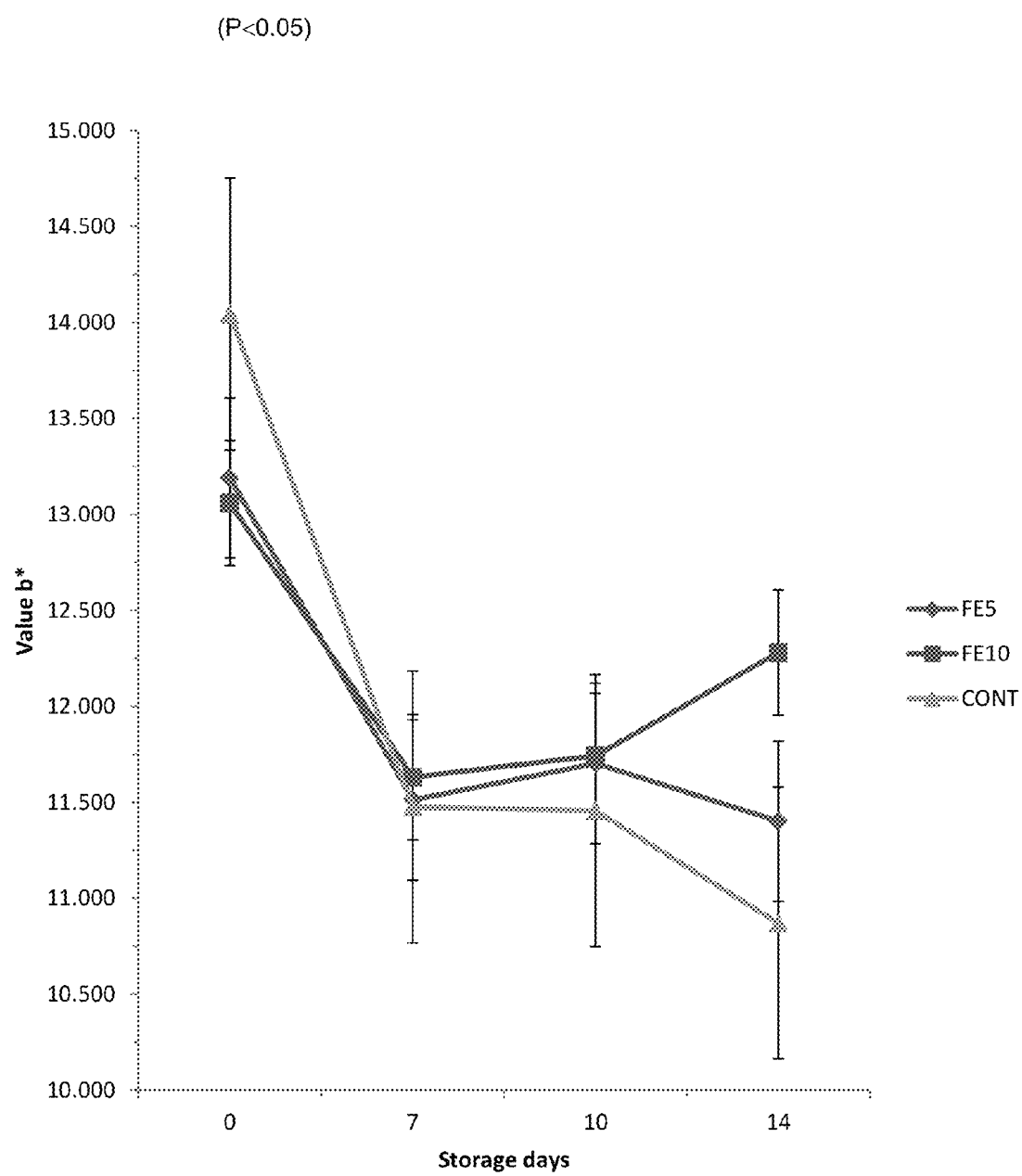
FIG. 5. Performance parameter b* color of beef during refrigerated storage at 4° C.

FIG. 3 shows the values of a* parameter (red trend). There were differences (P<0.05) only due to storage time. A reduction of this parameter was observed as time cooling progressed. The meat presented initial values of a* between 20 and 22 and on day 14 the values were between 12 and 15. Note that although no treatment effect (P>0.05) was presented, at the 14th storage control group showed lower levels of a*, while meat from FE5 treatment had the highest values.

For its part, the color differential* (Δa*) was affected by storage time and treatments (P<0.05). It was observed that the meat was gradually losing the red color over time. With regard to treatments, the flesh of animals supplemented with 5 or 10 ppm/day of FE was that kept more stable red color, because the 14th of storage only changed by about 5.5 units compared to baseline, while the meat Control group lost about 9 units (P<0.05). These results indicated that supplementation of FE at any dose allowed to reduce the loss of red meat during refrigerated shelf, and antioxidant capacity of this compound was shown, which has a favorable impact on the meat industry, from the economic point of view.

For the b* variable (FIG. 5) no differences between treatments (P>0.05) were presented; however there is an effect due to the time (P<0.05) noticing higher b* values on day 0 with respect to the days 7, 10 and 14 storage, which decreased about 2 units of the value b*.

Figure 6:
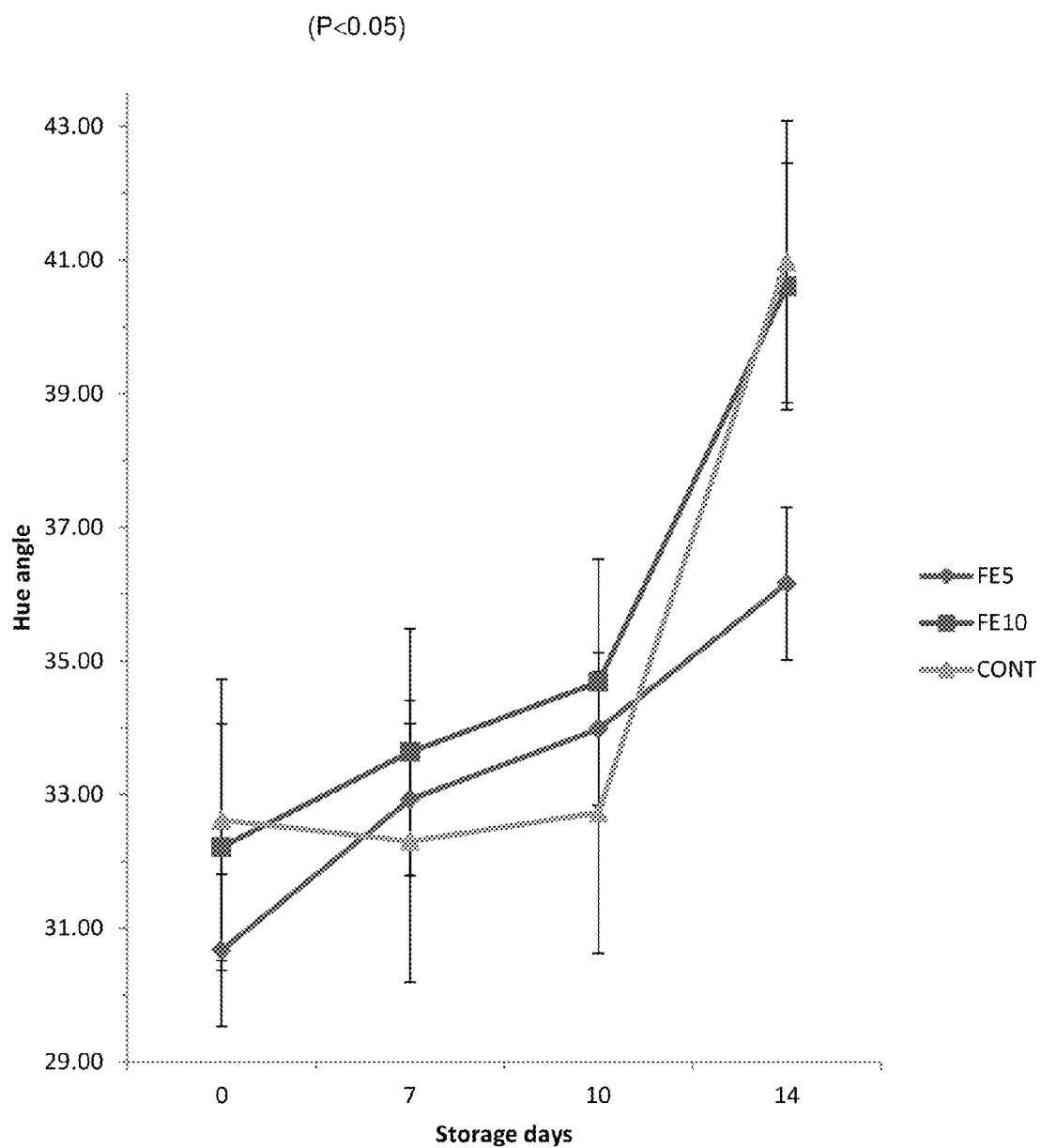
FIG. 6. Behavior hue angle parameter of beef during refrigerated storage at 4° C.

The hue angle behavior shown in FIG. 6. Differences between treatments (P>0.05) were not found; however, over time on days 0, 7 and 10, a meat with a hue angle closer to the strong red color of beef (30-34 degrees) it was observed, whereas on day 14 the values were increased for all treatments and were close to 40° (P<0.05). Although was not significant the effect of treatments, it appreciated that meat FE5 treatment presented a more stable hue angle.

Lipid Oxidation and Percentage of Metmyoglobin

Figure 7:
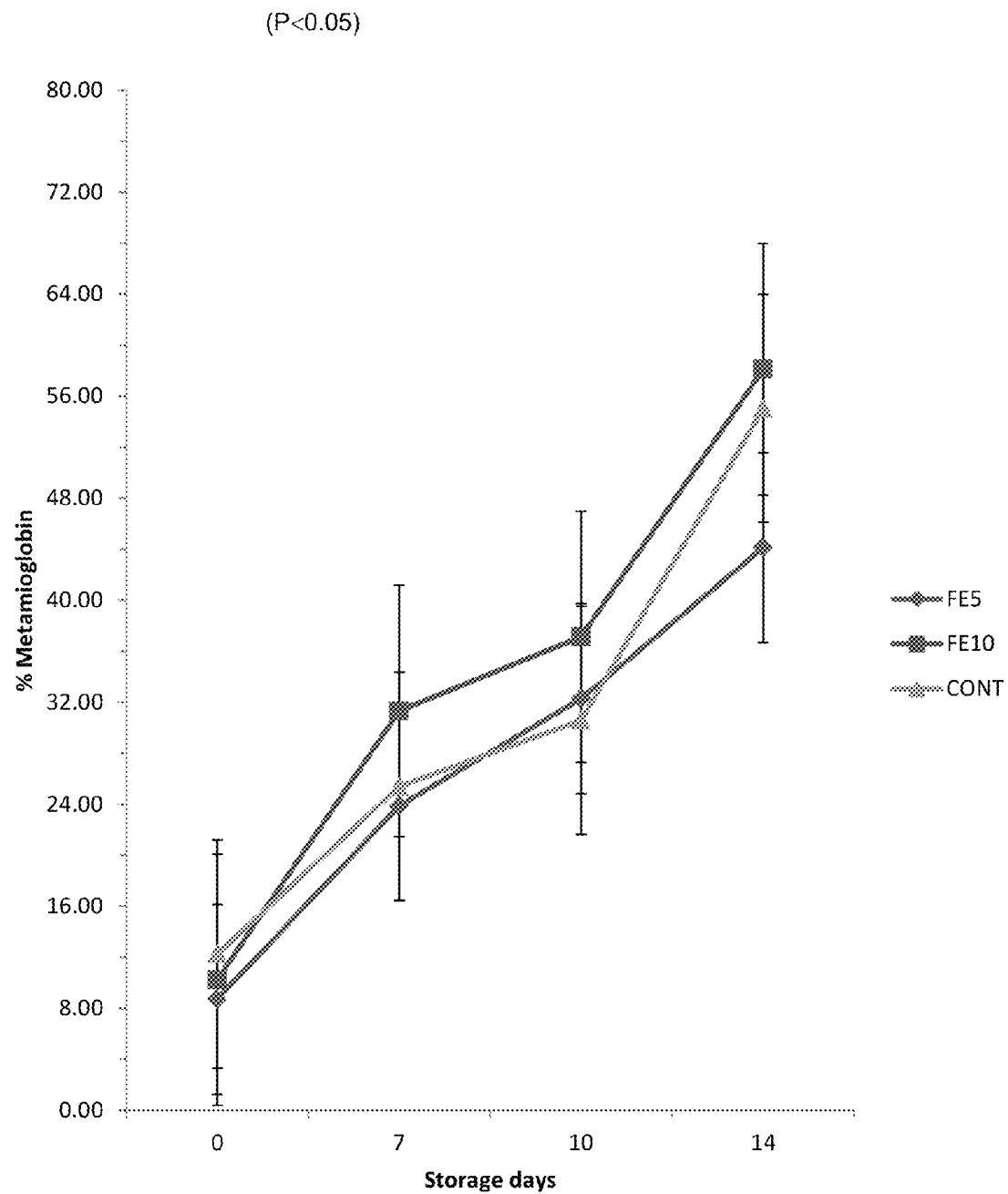
FIG. 7. Percentage of formation of metmyoglobin in beef during refrigerated storage at 4° C.

In FIG. 7 the behavior of metmyoglobin formation meat through storage is shown. A significant effect of storage time and the treatments (P<0.05) was observed. The meat of all treatments initially presented metamioglobin rates around 9% and was increasing up to values between 50 and 55% at the end of storage. As for the effect of the treatments, dietary supplementation of 5 ppm FE, caused a reduction in the formation of metmyoglobin in meat, compared to the values observed in the control treatments meat and FE10 (P<0.05). The ability of FE5 treatment to inhibit the formation of metmyoglobin in meat, also coincides with the results of the Δa* variable (changes in red), because it was the same treatment that kept the meat with lower values of Δa*. These results indicate that supplementation FE to 5 ppm, showed an ability to inhibit the protein oxidation, and this would result in minor changes to the red color of the meat during refrigerated marketing.

Figure 8:
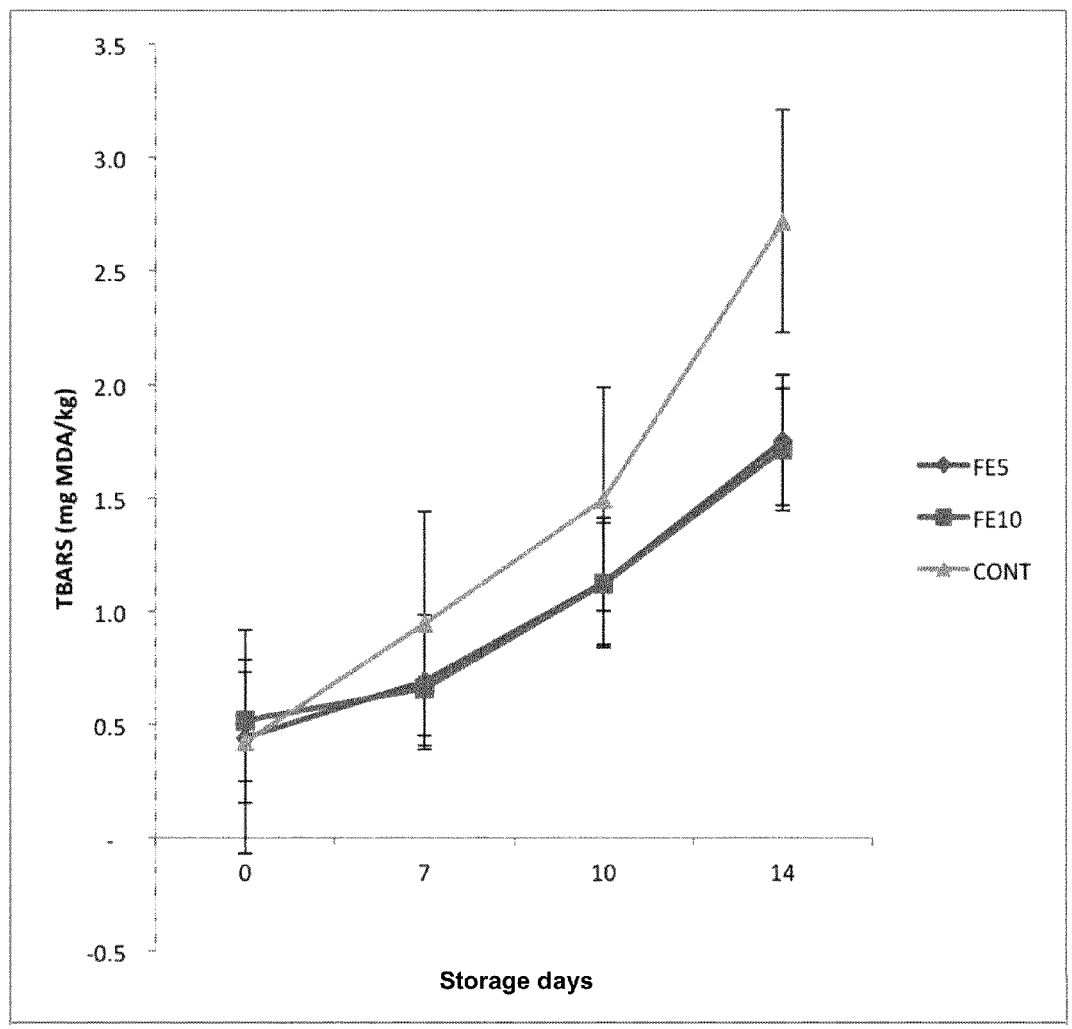
FIG. 8. TBARS values (mg malonaldehyde/kg muscle) in beef during refrigerated storage at 4° C.

Chemical deterioration, particularly lipid oxidation is a limiting factor in shelf life of meat, whereby the method is a viable TBARS measuring technique shelf life. In FIG. 8 the behavior of lipid oxidation of meat over time is observed. An effect of storage time for this variable (P<0.05) was observed. Higher values than 1.4 mg of malondialdehyde (MDA) per kg meat are taken as a reference to indicate that the meat can be perceived by the consumer as oxidized.

As already mentioned above, this example is illustrative only as to one embodiment of the present invention, therefore all those obvious modalities related to such invention fall within the protection scope of this invention.

Literature Cited

AMSA. (1995). *Research guidelines for cookery, sensory evaluation and instrumental tenderness measurements of fresh meat*, American Meat Science Association. Chicago, Ill., USA.

AMSA. (2012). *Research guidelines for cookery, sensory evaluation, and instrumental tenderness measurements of fresh meat*. American Meat Science Association. Chicago, Ill. USA.

Avendaño, L., Torres, V., Meraz, F., Pérez, C., Figueroa, F., & Robinson, P. (2006). Effects of two b-adrenergic agonists on finishing performance, carcass characteristics, and meat quality of feedlot steers. *Journal of animal science*, 84, 3259-3265.

Caicedo, R., Torres, A., Bustamante, Y., Paz, M., Ramirez, M., & Hernández, S. (2011). Efectos de los Beta-agonistas (clenbuterol), en las actividades fisiohepáticas y reproductivas en rumiantes. *Sitio Argentino de Producción Animal*, 1-6.

Eng, K. (2000). Choices of implants, implant strategies increases again Feedstuffs. 72, 10.

McLelland, M. R., Lind, L. R., & Kime, R. W. (1995). Hue angle determinations and statistical analysis for multiquadrant Hunter L*a*b* Data. *Journal of Food Quality*, 18: 235-240

Nirmal, N. P., & Benjakul, S. (2009). Effect of ferulic acid on inhibition of polyphenoloxidase and quality changes of Pacific white shrimp (*Litopenaeus vannamei*) during iced storage. *Food Chemistry*, 116(1), 323-331.

Pfalzgraf, A., Frigg, M., & Steinhart, H. (1995). Alpha tocopherol contents and lipid oxidation in pork muscle and adipose tissue during storage. *Journal of Agricultural and Food Chemistry*, 43, 1339-1342.

Platt, J. P., Anderson, M. J., & Johnson, B. J. (2012). *The effect of ferulic acid on myogenic regulators of growth in bovine satellite cells*. (Research report confidential to Laboratorios Minkab S. A. de C. V.): Texas Tech University.

Pollorena L. G. (2012). Capacidad antioxidante y antimicrobiana de extractos de hojas de Agave angustifolia Haw y su efecto sobre la calidad de hamburguesas de res. Tesis de Maestría en Ciencias. Centro de Investigación en Alimentación y Desarrollo A. C. Hermosillo, Sonora, Mexico.

Sánchez, D., Galindo, J., Ayala, C. M., & Assaf, M. A. (2011). Efecto del ácido ferúlico sobre el espesor de la grasa dorsal en cerdos. *Centro Universitario de Ciencias Biológicas de Guadalajara. F. E. S. MINKAB*.

Serna, P. (2012). *Impacto de la suplementación de ácido ferúlico sobre la calidad de la carne de bovinos comerciales*. Unpublished Tesis de Maestria en Ciencias, Centro de Investigación en Alimentación y Desarrollo, Hermosillo, Sonora.

Stewart, M. R., Zipser, M. W., & Watts, B. M. (1965). The Use of Reflectance Spectrophotometry for the Assay of Raw Meat Pigments. *Journal of Food Science*, 30(3), 464-469.

Strydom, P., Frylinck, L., Montgomery, J., & Smith, M. F. (2009). The comparison of three β-agonists for growth performance, carcass characteristics and meat quality of feedlot cattle. *Meat Science*, 81(3), 557-564.

Sutton, D. S., Ellis, M., Lan, Y., McKeith, F. K., & Wilson, E. R. (1997). Influence of slaughter weight stress gene genotype on the water holding capacity and protein gel characteristics of three porcine muscles. *Meat science*, 46, 173-180.

The invention claimed is:

1. A feed premix to a bovine animal, comprising an amount of ethyl ferulate and a food grade excipient.

2. The feed premix according to claim 1, wherein the bovine animal is selected from a subspecies: *Bos primigenius taurus* y *Bos primigenius indicus*.

3. A feed formulation for a bovine animal comprising an amount of ethyl ferulate and food.

4. The feed formulation of claim 3, wherein the ethyl ferulate is added pure or premixed.

5. The feed formulation according to claim 4 wherein the premixed ethyl ferulate comes from a feed premixture to a bovine animal, comprising an amount of ethyl ferulate and a food grade excipient.

6. The feed formulation according to claim 3, wherein the amount of ethyl ferulate is 100 to 600 g/TM.

7. The feed formulation of claim 6, wherein the amount of ethyl ferulate is 200 to 500 g/TM.

8. The feed formulation according to claim 3, wherein the bovine animal is selected from the subspecies: *Bos primigenius taurus* y *Bos primigenius indicus*.

9. The feed formulation as claimed in claim 3, wherein the food is a balanced food, balanced fattening food and/or concentrated food.

10. A method for improving the efficiency of production of meat from a bovine animal, comprising providing daily bovine animals a feed formulation comprising a dose of ethyl ferulate, during the last days of a fattening phase of the bovine animal.

11. The method according to claim 10, wherein the dose of ethyl ferulate is 5 to 10 ppm.

12. The method according to claim 11, wherein the dose of ethyl ferulate is 10 ppm.

13. The method according to claim 10, wherein the bovine animal is selected from the subspecies: *Bos primigenius taurus* y *Bos primigenius indicus*.

14. The method according to claim 10, wherein the final days of the fattening phase are 20-40 days.

15. The method according to claim 14, where the last days of the fat phase are 30 days.

16. The method according to claim 10, wherein the ferulate acetate is added pure or premixed at feed formulation.

17. The method according to claim 16, wherein the premixed ethyl ferulate comes from a feed premixture to a bovine animal, comprising an amount of ethyl ferulate and a food grade excipient.

18. The feed formulation according to claim 3, wherein the bovine animal is selected from the subspecies: *Bos primigenius taurus* y *Bos primigenius indicus*.

* * * * *